United States Patent [19]

Lee et al.

[11] Patent Number: 4,462,941

[45] Date of Patent: Jul. 31, 1984

[54] DYNORPHIN AMIDE ANALOGS

[75] Inventors: Nancy M. Lee; Horace H. Loh, both of San Francisco; Jaw-Kang Chang, San Carlos, all of Calif.

[73] Assignee: The Regents of the University of California, Berkeley, Calif.

[21] Appl. No.: 387,005

[22] Filed: Jun. 10, 1982

[51] Int. Cl.$^3$ .................... C07C 103/52; A61K 37/00
[52] U.S. Cl. ........................... 260/112.5 R; 424/177
[58] Field of Search .................. 424/177; 260/112.5 R

[56] References Cited

U.S. PATENT DOCUMENTS 4,361,553 11/1982 Loh et al. ........................... 424/177
4,396,606 8/1983 Goldstein ....................... 260/112.5 R

FOREIGN PATENT DOCUMENTS 0029300 5/1981 European Pat. Off. .

OTHER PUBLICATIONS

Chem. Abstr., vol. 97, (1982), 120652p, 175904c.
Chem. Abstr., vol. 94, (1981), 2025508.
Chem. Abstr., vol. 93, (1980), 231390p.
Goldstein et al., *Proc. Natl. Acad. Sci. USA*, vol. 76, No. 12, pp. 6666–6670, (1979).
Herman et al., *Life Sciences*, vol. 27, pp. 883–892, (1980).
Friedman et al., "Dynorphin: A Possible Modulatory Peptide on Morphine or β-Endorphin Analgesia in Mouse", *Europ. J. Pharmacology*, (in press).
Tulunay et al., *J. Pharm Exp. Ther.*, 190, pp. 395–400, (1974).
Litchfield et al., *J. Pharmacol. Exap. Ther.*, 96:99–113, (1949).
D'Amour et al., *J. Pharmac. Exp. Ther.*, 72, pp. 74–79, (1941).
Way et al., *J. Pharmac. Exp. Ther.*, 167, pp. 1–8, (1969).
Tulunay et al., *Advances in Endogenous and Exogenous Opioids Abstracts*, p. 123, (Jul. 26–30, 1981).
Chavkin et al., *Proc. Natl. Acad. Sci. USA*, vol. 78, No. 10, pp. 6543–6547, (Oct. 1981).
Tulunay et al., *The Journal of Pharmacology and Experimental Therapeutics*, vol. 219, No. 2, pp. 296–298, (1981).
Tulunay et al., *European Journal of Pharmacology*, vol. 76, pp. 235–239, (1981).
Chavkin et al., *Nature*, vol. 291, No. 816, pp. 391–393, (Jun. 1981).
Zwiers et al., *Life Sciences*, vol. 28, No. 22, pp. 2545–2551, (1981).
Piercey et al., *European Journal of Pharmacology*, vol. 80, pp. 283–284, (1982).

*Primary Examiner*—Delbert R. Phillips
*Attorney, Agent, or Firm*—Majestic, Gallagher, Parsons & Siebert

[57] ABSTRACT

Dynorphin(1–13) has been previously reported to antagonize the analgesia induced by narcotics in naive hosts. Novel compounds are provided which differ from dynorphin(1–13) by neither potentiating nor antagonizing narcotics, such as morphine, in naive animals. In tolerant hosts the new compounds potentiate narcotic or peptide induced analgesia, and in addition are less susceptible to degradation than dynorphin(1–13).

Particularly preferred of the new compounds are polypeptides having ten amino acids with nitrogen containing moieties at both termini.

3 Claims, No Drawings

DYNORPHIN AMIDE ANALOGS

Preferred embodiments of the invention have the formula

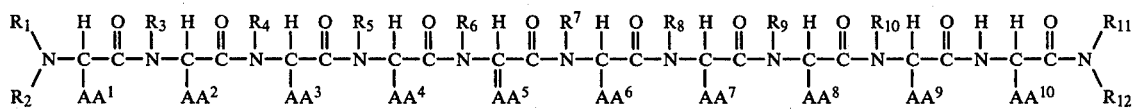

This invention was made with Government support under Grant Nos. DA-00564 and DA-02643 awarded by the Dept. of Health and Human Services. The Government has certain rights in this invention.

FIELD OF THE INVENTION

The present invention generally relates to dynorphin, and more particularly to dynorphin analogs useful with narcotic analgesics, such as opiate alkaloids, and peptide analgesics such as enkephalins and β-endorphin analogs.

BACKGROUND OF THE INVENTION

One of the plurality peptides to be recently discovered contains seventeen amino acids and is generally referred to as dynorphin. Dynorphin has been discovered to have potent agonist properties in guinea pig ileum and mouse vas deferens. Both dynorphin(1–13) and dynorphin(1–17) have been sequenced and synthesized. The synthetic dynorphin(1–13) product has been found to be as potent in bioassays as the naturally occurring peptide, but has been shown to be relatively weak in producing analgesia in studies with mice.

It has been reported that dynorphin(1–13), but not the shorter fragment, dynorphin(1–9), has significant effects on opiate and β-endorphin-induced analgesia in naive animals. The studies have suggested that dynorphin(1–13) may interact with other analgesic opioids. Thus, it has been recently shown that dynorphin(1–13) appears to interact with morphine to significantly attenuate, or inhibit, the analgesia produced by morphine in naive animals.

SUMMARY OF THE INNVENTION

It has been discovered that amide analogs of dynorphin having at least ten amino acids (but less than 13), and particularly dynorphin(1–10) amide, do not antagonize narcotic analgesics in naive animals as do dynorphin, dynorphin(1–13) and dynorphin(1–13) amide. Further, dynorphin amide analogs have been found to potentiate the analgesic effect in tolerant hosts. In addition, dynorphin(1–10) amide and certain amide analogs thereof are less quickly metabolized by the host, and thus smaller doses than with dynorphin(1–13) can be administered in therapeutic applications.

Therapeutic uses of the dynorphin(1–10) amides include administration to a host tolerant to a narcotic analgesic. Lower doses of a narcotic analgesic, for example an opiate alkaloid such as morphine, may be used for patients requiring chronic treatment with narcotics to ease pain, such as terminal cancer patients, or lower doses of a narcotic such as methadone may be used in treating narcotics addicts. As a consequence, the various, known side effects, such as respiratory depression and constipation, which result from chronic treatment with high doses of narcotics, can be lessened.

Furthermore, dynorphin amide analogs can be used for the treatment of narcotic withdrawal.

where $R_1$ and $R_2$ are hydrogen, alkyl, allyl, formyl, or acetyl, $R_{11}$ and $R_{12}$ are hydrogen, alkyl or allyl, $R_3$–$R_{10}$ are hydrogen or $-(CH_2)_n$, where $n=1$ or 2, $AA^1$ is tyrosine, $AA^2$ and $AA^3$ are glycine, $AA^4$ is phenylalanine, $AA^5$ is leucine, $AA^6$ and $AA^7$ are arginine, $AA^8$ is isoleucine, tyrosine or lysine, $AA^9$ is arginine or proline, $AA^{10}$ is proline.

BEST MODE OF PRACTICING THE INVENTION

The present invention is useful with substantially all narcotic analgesics. For example, the present invention is useful with the various alkaloids of opium such as morphine, morphine salts (such as morphine hydrobromide, morphine hydrochloride, morphine mucate, morphine oleate, morphine N-oxide and morphine sulfate), and morphine analogs such as normorphine, diacetyldihydromorphine, diacetylmorphine hydrochloride, codeine and diacetylmorphine (heroin). Other widely used narcotic analgesics with which the present invention may be used include alphatrodine, methadone, merperidine, leverthanol, propoxyphene, fentanyl, oxymorphone, anileridine and metopon. Uses can be extended to the peptide analgesics, such as enkephalins and β-endorphin analogs.

As is well known, continued use of these narcotic analgesics leads to habituation or addiction, and use of one leads to cross-tolerance for the others. However, despite their abuse potential, these narcotic analgesics have therapeutic uses, for example with patients requiring chronic treatment to ease pain.

Even in such therapeutic uses, though, patients develop increasing tolerances to these narcotic analgesics, so that increasingly potent doses are required to achieve relief from pain. Undesirable side effects then tend to develop to the large, chronic doses of the narcotic analgesics.

The agonistic actions and dependence-producing properties of narcotic analgesics can be, and are, studied in various mammalian species besides humans, since practical and governmental considerations frequently require that studies be first done in small rodents and/or monkeys before the analgesic properties of pharmaceuticals are tested with humans. To the present, however, all drugs that have morphine-like properties in mammals other than man have been found to be morphine-like in man, and a variety of analgesic assays have been developed with animals which have gained widespread acceptance for predicting properties in humans.

Therapeutic uses of the inventive compounds may be in conjunction with narcotic analgesics, and more preferably with opitae alkaloids. Unless otherwise noted, use of the term "dynorphin" alone herein means the naturally occurring or synthetically sequenced heptadecapeptide, and use of the term "dynorphin" with an indication such as (1–10) or (1–13) means those polypeptides having the sequence of the ten amino acids of the naturally occurring heptadecapeptide (e.g. dynorphin(1-10)) or the thirteen amino acids of the naturally occurring heptadecapeptide.

The first thirteen amino acids of dynorphin, or dynorphin(1-13), have the sequence:

TYR—GLY—GLY—PHE—LEU—ARG—ARG—ILE—ARG—PRO—LYS—LEU—LYS.
  1     2     3     4     5    6     7    8    9    10   11    12   13

The N-terminal end contains Leu-enkephalin (those amino acids numbered 1-5), followed by the C-terminal extension (those amino acids numbered 6-13). The inclusion of Leu-enkephalin has been believed to be necessary as a biological "homing device" for activity, and the length of extension beyond Leu-enkephalin has been believed to be critical for its potency.

Novel dynorphin polypetide amide analogs have been synthesized having at least ten amino acids (but less than thirteen) which differ from dynorphin and dynorphin(1-13) by neither potentiating nor antagonizing narcotic analgesia in naive hosts. In tolerant hosts, these analogs are more potent and selective than dynorphin(1-13) in potentiating narcotic analgesia.

The compounds of the present invention have at least ten amino acids linked sequentially by peptide bonds, with the five amino acids (or structurally similar moieties, such as d or l dopa at position 1) from the N-terminal end are the same as, or mimic, Leu-enkephalin, whereas amino acids 6-10 substantially constitute a basic portion of the molecule (with basic, or basic and neutral moieties). The dynorphin amide analogs of the invention with amino acids numbered beginning from an N-terminal end, or amino group, are generally illustrated by FIG. I below.

$AA^6$ and $AA^7$ may be a basic amino acid in either the d or l form (e.g., arginine, lysine or histidine), homoarginine or ornithine, more preferably arginine.

$AA^8$ may be neutral or basic amino acids in the d or l form, leucine or isoleucine, more preferably tyrosine, isoleucine, or lysine.

$AA^9$ may be a basic amino acid in either the d or l form, homoarginine, ornithine, or proline, more preferably arginine or proline.

$AA^{10}$ may be a basic amino in either the d or l form, proline, or a propline analog (such as thioproline, 3,4,-dehydroproline, 4-hydroxyproline, or pipecolic acid), more preferably proline or lysine.

Particularly preferred are:

TYR-GLY-GLY-PHE-LEU-ARG-ARG-ILE-ARG-PRO
 1    2    3    4    5    6    7    8    9   10 where the carbonyl carbon at the proline terminus is amidated (sometimes referred to herein as "dynorphin(1-10) amide");

TYR-GLY-GLY-PHE-LEU-ARG-ARG-LYS-ARG-PRO
 1    2    3    4    5    6    7    8    9   10 where the carbonyl carbon at the proline terminus is amidated (sometimes hereinafter referred to as the "formula 1 analog");

FIG. I

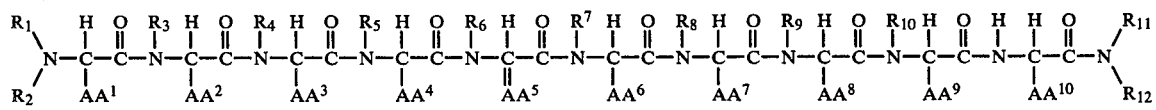

TYR-GLY-GLY-PHE-LEU-ARG-ARG-LEU-ARG-PRO
 1    2    3    4    5    6    7    8    9   10 where the carbonyl carbon at the propline terminus is amidated (sometimes hereinafter referred to as the "formula 2 analog").

Preparation is illustrated by Example I, below.

EXAMPLE I

Dynorphin(1-10)-$NH_2$ was synthesized on a solid support of Boc-Pro-BHA (Benzhydrylamine) resin (2 mM/4.5 g of resin). With the Merrifield procedure on a Peninsula manual solid-phase peptide synthesizer, the corresponding Boc-protected amino acids were added respectively onto the Boc-Pro-BHA resin: Arg(Tos), Ile, Arg(Tos), Arg(Tos), Leu, Phe, Gly, Gly and Tyr(o-Br-Z). A 5.0 molar excess of each protected amino acid was used. The success of the coupling reaction was monitored by the semiquantitive ninhydrin test. The following steps were employed to couple the Boc-protected amino acid to Boc-Pro-BHA resin:

1. Washing with $CH_2Cl_2$ (3×100 ml.)
2. Prewashing with 33% TFA in $CH_2Cl_2$ with 1% indole. (1×100 ml.)
3. Deprotection with 33% TFA in $CH_2Cl_2$ with 1% indole. (1×100 ml.), 20 min.

$R_1$ and $R_2$ are hydrogen, alkyl, allyl, or acyl (such as formyl of acetyl); $R_{11}$ and $R_{12}$ are hydrogen, alkyl, a benzylic group (substituted or unsubstituted), one of $R_{11}$ and $R_{12}$ may be a nitrogen containing moiety such as hydrazide and the other hydrogen, or one of $R_{11}$ and $R_{12}$ may be a basic or neutral amino acid or a basic or neutral dipeptide and the other hydrogen or an alkyl group; $R_3$-$R_{10}$ are hydrogen or an alkyl group of not more than about four carbons (branched or unbranched), more preferably methyl or ethyl; and, the sequential amino acids are as follows.

$AA^1$ may be tyrosine, m-tyrosine or dopa (d or l form), more preferably tyrosine.

$AA^2$ and $AA^3$ may be glycine or other neutral amino acids in either the d or l form (e.g., serine, threonine, cysteine, tyrosine, asparagine, methionine and glutamine) or α-amino isobutyric acid (AIB), more preferably glycine.

$AA^4$ may be phenylalanine, α-alkylated phenyl alanine (such as α-methyl phenylalanine), p-halophenylalanine, or tyrosine, more preferably phenylalanine.

$AA^5$ may be leucine, isoleucine or valine, more preferably leucine.

4. Washing with $CH_2Cl_2$ (1×100 ml.)
5. Washing with EtOH (1×100 ml.)
6. Washing with $CH_2Cl_2$ (2×100 ml.)
7. Prewashing with 10% $Et_3N$ in $CH_2Cl_2$ (1×100 ml.)
8. Neutralization with 10% $Et_3N$ in $CH_2Cl_2$ (1×100 ml.), 10 min.
9. Washing with $CH_2Cl_2$ (3×100 ml.)
10. Protected amino acid (5.0 molar excess) in DMF (10 ml.) and $CH_2Cl_2$ (50 ml.) was added.
11. DCC in $CH_2Cl_2$ (0.5M, 20 ml.) was added and the reaction time was up to three hours.
12. Washing with $CH_2Cl_2$ (3×100 ml.)

The resulting protected Boc-Tyr(O-Br-Z)-Gly-Gly-Phe-Leu-Arg(Tos)-Arg(Tos)-Ile-Arg(Tos)-Pro-BHA resin was washed well with 33% TFA in $CH_2Cl_2$, $CH_2Cl_2$ and MeOH respectively. After drying in vacuo overnight, the peptide resin was cleaved by HF (30 ml./g. of resin) in the presence of anisole (3 m./g. or resin) for one hour at 0° C. The reaction mixture was dried in vacuo and washed with anhydrous ether. The desired peptide was dissolved in 10% HOAc and the resin was filtered off. The filtrate was lypohilized to give crude dynorphin(1-10)-$NH_2$. This peptide was purified by partition chromatography using n-BuOH:pyridine:$H_2O$ (11:5:3) as eluting solvent and CM ion-exchange chromatography to afford the pure dynorphin(1-10)-$NH_2$.

The best mode contemplated for carrying out the present invention comprises administering a dose of dynorphin(1-10) amide or one of the inventive analogs thereof to a host in conjunction with administering a dose of a narcotic analgesic, wherein the administration of dynorphin(1-10) amide or analog thereof is within at least about 30 minutes of the narcotic analgesic dose. Preferably, the administering is by administering a single, admixed dose where the narcotic analgesic, is morphine, a morphone analog, or a morphine salt, or other peptide analgesics.

Where the administering of narcotic analgesic is morphine and is to a naive patient, a normal dosage is on the order of about 5 mg i.v., assuming a body weight of about 70 kg. It is believed a suitable dose of the dynorphin(1-10) amide or analog thereof, administered in conjunction with the analgesic, is from about 60-200 μg per kg body weight. Although the dynorphin(1-10) amide or anlog thereof does not potentiate the narcotic analgesic in an initially naive host (nor does it antagonize), as the patient continues in an extended treatment with narcotics to ease pain, the amount of narcotic required to produce a sufficient level of analgesia over the treatment period will be less than without use of dynorphin(1-10) amide or analog thereof in conjunction with the narcotic. As a consequence, the various undesirable side effects of repeated, high doses of narcotics, can be lessened.

The dosage in tolerant patients may be determined as follows. A first, or sufficient, dose of the narcotic analgesic is determined which would be sufficient to produce analgesia in the host. However, instead of administering the sufficient dose, a predetermined dose of the narcotic analgesic is administered. This predetermined, or second, dose includes less of the narcotic analgesic than would be sufficient to produce analgesia in the host. The actually administered dose of narcotic analgesic is supplemented with dynorphin(1-10) amide or analog thereof. The supplementation is preferably sufficient to produce a level of analgesia in the host which is substantially equivalent to the level of analgesia were solely the narcotic analgesic to have been administered.

As may be understood, the first or sufficient dose, the lower, second dose, and the supplementing dose will vary depending upon the patient's particular level of tolerance to the narcotic analgesic, and will normally be determined by the treating physician.

Although the best mode contemplated for practice of the present invention is in using the inventive compounds in conjunction with a narcotic analgesic in order to reduce the amount of narcotic analgesic administered per dose, it is also believed that another therapeutic method of use is in treating addicts to substantially block withdrawal symptoms.

The following experimental methods, materials and results are described for purposes of illustrating the present invention. However, other aspects, advantages and modifications within the scope of the invention will be apparent to those skilled in the art to which the invention pertains.

Male simonesen ICR mice (Gilroy, CA) weighing between 20-25 g were housed for at least one day prior to experimentation, and used within 5 days. Each mouse was used only once.

Analgesia was measured by the tail-flick method of D'Amour and Smith, *J. Pharmac. Exp. Ther.*, 72, pp. 74–79 (1941), incorporated herein by reference, as modified by Tulunay and Takemori, *J. Pharmac. Exp. Ther.*, 190, pp. 395–400 (1974), incorporated herein by reference. For $ED_{50}$ (e.g., effective dose for 50% of the test group) determinations, the animals' responses were made quantal by establishing an endpoint which represented a significant increase in reaction time. The endpoint was an increase in the reaction time of an individual animal of greater than 3 SD (e.g., standard deviation) of the control mean reaction time for all animals used in the assay. The usual control mean reaction time was 3.1±0.05 sec. Nonresponding animals were removed from the heat stimulus when reaction times exceeded 10 sec. to avoid the tail damage.

Drugs were injected 30 min. prior to testing, unless otherwise indicated. Morphine was injected subcutaneously (s.c.) whereas the polypeptides were injected intracerebroventricularly (i.c.v.) in 4 ml. saline.

The animals were separated into two groups. The one group was morphine tolerant (e.g., addicted); the other group was naive (e.g., not addicted). Tolerance was established in each host of the one group by implanting morphine pellets, 75 mg base, subcutaneously by the method of Way et al, *J. Pharmac. Exp. Ther.*, 167, pp. 1–8 (1969), incorporated herein by reference. The pellets were removed 72 hr. after implantation, and the mice were tested for morphine tolerance 6 hr. later.

At least 30 animals were used from both the morphine tolerant group and from the other, or naive, group to determine each dose-response curve and $ED_{50}$ values of each treatment. The $ED_{50}$ values, their 95% confidence limits and significance of the potency ratio between two $ED_{50}$ values were determined by the method of Litchfield and Wilcoxon, *J. Pharmac. Exp. Ther.*, 96: 99–113 (1949), incorporated herein by reference.

The drugs used in these experiments were morphine sulfate (Mallinckrodt Chemical Works, St. Louis, MO) and β-endorphin (a gift from Dr. N. Ling, Salk Institute, San Diego, CA).

Examples II and III, below, illustrate the effect of dynorphin(1-13) in conjunction with morphine and β-endorphin induced analgesia, respectively, in animals from the morphine tolerant group. Example IV is described for comparison with Examples II and III.

Although the dynorphin(1–13) was administered i.c.v. in the Examples II–IV, intraveneous (i.v.) or s.c. administration yielded similar results with comparable doses.

EXAMPLE II

Over 90 morphine tolerant animals were treated with various amounts of morphine sulfate s.c., either alone or in the presence of various amounts of dynorphin(1–13) i.c.v., and then tested for analgesia. Results of these tests are summarized by the data below, taken from three dose-response curves (each determined from at least 30 animals), one with no dynorphin(1–13) having been administered, and two with dynorphin(1–13) having been administered in conjunction with morphine.

| Morphine (mg/kg) | Dynorphin (μg) | Analgesia (%) |
|---|---|---|
| 25 | — | — |
| 60 | — | 40 |
| 80 | — | 90 |
| 15 | 10 | 10 |
| 25 | 10 | 40 |
| 60 | 10 | 85 |
| 15 | 20 | 30 |
| 25 | 20 | 70 |
| 40 | 20 | 100 |

As may be seen from the test results summarized above, dynorphin(1–13) potentiated the morphine effect in tolerant animals. Thus, the $ED_{50}$ of morphine was shifted from about 60 (mg/kg) to about 29 in the presence of 10 μg dynorphin(1–13), and from about 60 (mg/kg) to about 18 in the presence of 20 μg dynorphin(1–13).

EXAMPLE III

Over 90 morphine tolerant animals were treated with various amounts of β-endorphin i.c.v., either alone or in the presence of various amounts of dynorhin(1–13) i.c.v. and then tested for analgesia. Results from these tests are summarized by the data below, taken from three dose-response curves (each determined from at least 30 animals), one with no dynorphin(1–13) having been administered, and two with dynorphin(1–13) having been administered in conjunction with β-endorphine.

| β-Endorphin(μg/mouse) | Dynorphin(μg) | Analgesia (%) |
|---|---|---|
| 1 | — | 10 |
| 2 | — | 40 |
| 6 | — | 100 |
| 0.5 | 10 | 10 |
| 1 | 10 | 60 |
| 2 | 10 | 80 |
| 0.25 | 20 | 20 |
| 0.5 | 20 | 40 |
| 1 | 20 | 80 |

As may be seen from the test results summarized above, dynorphin(1–13) potentiated the β-endorphin effect. Thus, the $ED_{50}$ of β-endorphin was shifted from about 2.25 μg/mouse i.c.v. to about 1.00 and about 0.55 in the presence of 10 to 20 μg dynorphin(1–13), respectively.

For comparison, Example IV, below, illustrates the effect of dynorphin(1–13) in conjunction with morphine induced analgesia in animals from the naive group.

EXAMPLE IV

Over 90 naive animals were treated with morphine sulfate s.c., either alone or in the presence of various amounts of dynorphin(1–13) i.c.v., and then tested for analgesia. Results of these tests are summarized by the data below taken from three dose-response curves (each determined from at least 30 minutes), one with morphine having been administered, and two with dynorphin(1–13) having been administered in conjunction with morphine.

| Morphine (mg/kg) | Dynorphin (μg) | Analgesia (%) |
|---|---|---|
| 2 | — | 10 |
| 4 | — | 30 |
| 5 | — | 60 |
| 7.5 | — | 80 |
| 3.75 | 10 | 10 |
| 10 | 10 | 60 |
| 15 | 10 | 100 |
| 7.5 | 20 | 10 |
| 10 | 20 | 30 |
| 20 | 20 | 60 |
| 40 | 20 | 100 |

As may be seen from the test results summarized above, dynorphin(1–13) significantly inhibited the morphine induced analgesia in a dose related manner, and shifted the morphine-response curve to the right. Thus, the $ED_{50}$ of morphine administered s.c. was shifted from about 4.9 mg/kg to about 8.4 and about 14.5 in the presence of 10 and 20 μg dynorphin(1–13), respectively.

A similar effect was observed on analgesia induced by i.c.v. β-endorphin. However, dynorphin(1–9) up to 40 μg, or -(6–13) up to 80 μg, were inactive in inhibiting morphine induced analgesia in similar experiments.

As may be seen by comparing the data from Example IV with Examples II and III, instead of inhibiting a morphine induced analgesia (as occurred in the naive animals of Example IV), administering dynorphin to morphine tolerant animals potentiated the morphine effect. This shift in the morphine $ED_{50}$ was not due to dynorphin's own effect, since dynorphin up to 50 μg/mouse still showed no analgesic potency. Similar results occurred with β-endorphin induced analgesia. In both the morphine and β-endorphin cases, the potentiation was dose-related.

Example V, below, illustrates the effect of dynorphin(1–10) amide in conjunction with morphine induced analgesia in naive animals.

EXAMPLE V

A group of at least 30 naive animals were treated with morphine sulfate s.c., either alone, in the presence of various amounts of dynorphin(1–10) amide, or dynorphin (1–13) amide.

The treatment was repeated with another group of at least 30 naive animals, and single-blind experiments were run also to confirm results.

|  | i.c.v. (μg) | $ED_{50}$ |
|---|---|---|
| saline | | 4.7 (3.2–6.8) |
| dynorphin(1–10) amide | 20 | 5.0 (3.12–8.00) |
| dynorphin(1–10) amide | 10 | 4.3 (3.1–5.9) |
| dynorphin(1–10) amide | 50 | 4.4 (2.7–7.1) |

-continued

| | i.c.v. (μg) | ED$_{50}$ |
|---|---|---|
| dynorphin(1-13) amide | 10 | 14.0 (11.3-17.4) |

As may be seen by the test results summarized above, dynorphin(1-10) amide did not shift the morphine-response curve, and thus there was neither antagonism nor potentiation in naive animals. This is in contrast to the effect of dynorphin(1-13) amide with naive animals.

Example VI, below, illustrates the effect of dynorphin(1-10) amide, the formula 1 analog, the formula 2 analog, and amidated dynorphin(1-13) with morphine induced analgesia in tolerant animals.

EXAMPLE VI

A group of at least 30 tolerant animals were treated with morphine sulfate s.c., either alone or in the presence of the inventive dynorphin amide analogs. In addition, dynorphin(1-13) amide was synthesized and run for comparison.

The treatment was repeated with another group of at least 30 tolerant animals, and single blind experiments were also run to confirm results.

| | μg | ED$_{50}$ |
|---|---|---|
| saline | | 41.5 (30.7-56.0) |
| dynorphin(1-10) amide | 20 | 9.9 (6.6-15.2) |
| formula 1 analog | 20 | 17.5 (13.4-22.9) |
| formula 2 analog | 20 | 23.0 (17.6-30.1) |
| dynorphin(1-13) amide | 50 | 10.8 (7.2-16.2) |

As may be seen from the test results summarized above, dynorphin(1-10) amide greatly potentiated the morphine induced analgesia (e.g., shifted the morphine-response curve to the left) in tolerant animals, (with the formula 1 and 2analogs also effecting potentiation, but to a lesser degree).

In tolerant hosts, dynorphin(1-13) amide also potentiated analgesia.

In other tests, dynorphin(1-10) amide was shown to be more potent than dynorphin(1-13) in inhibiting the twitch of the mouse vas deferens (IC$_{50}$ of dynorphin(1-10) amide=0.24 nM and IC$_{50}$ of dynorphin(1-13)=3.9 nM). Binding assays indicated the two opioid peptides have similar profiles in that they enhance dihydromorphine (DHM) binding in picomolar concentrations but displace DHM binding in nanomolar concentrations (IC$_{50}$ for dynorphin(1-10) amide=5 nM). In the mouse tail-flick assay, however, dynorphin(1-10) amide shows a more selective action on morphine-induced analgesia.

In sum, although dynorphin(1-10) amide has no significant analgesic activity by itself (unless given in huge doses where it tends to produce convulsions, and the like behavior), it differs from dynorphin(1-13) by neither potentiating nor antagonizing morphine in naive animals. In tolerant animals, on the other hand, dynorphin(1-10) amide appears to be a more potent and selective analog than dynorphin(1-13).

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A dynorphin analog having the sequence TYR-GLY-GLY-PHE-LEU-ARG-ARG-AA$^8$-AA$^9$-AA$^{10}$ wherein AA$^8$ is isoleucine, leucine or lysine, AA$^9$ is arginine or proline, AA$^{10}$ is proline and a carbonyl carbon at the AA$^{10}$ terminus is amidated.

2. A polypeptide having the sequence TYR-GLY-GLY-PHE-LEU-ARG-ARG-AA$^8$-ARG-PRO wherein the proline thereof is amidated and AA$^8$ is tyrosine, isoleucine or lysine.

3. The polypeptide as in claim 2 wherein AA$^8$ is isoleucine.

* * * * *